US00PP37686P2

(12) United States Plant Patent
van Swieten

(10) Patent No.: US PP37,686 P2
(45) Date of Patent: Sep. 8, 2026

(54) ***PHALAENOPSIS* PLANT NAMED 'PHA533378'**

(50) Latin Name: *Phalaenopsis hybrida*
Varietal Denomination: PHA533378

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/329,283

(22) Filed: Sep. 15, 2025

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

(56) References Cited

U.S. PATENT DOCUMENTS

PP28,944 P2 * 2/2018 Van Swieten ..... A01H 6/62
Plt./311

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'PHA533378', characterized by its upright plant habit; medium in height; moderately vigorous growth habit; sturdy flowering stems; freely flowering habit with typically two inflorescences developing per plant, each inflorescence with numerous flowers; and medium to broad white-colored flowers.

2 Drawing Sheets

Figure 1:
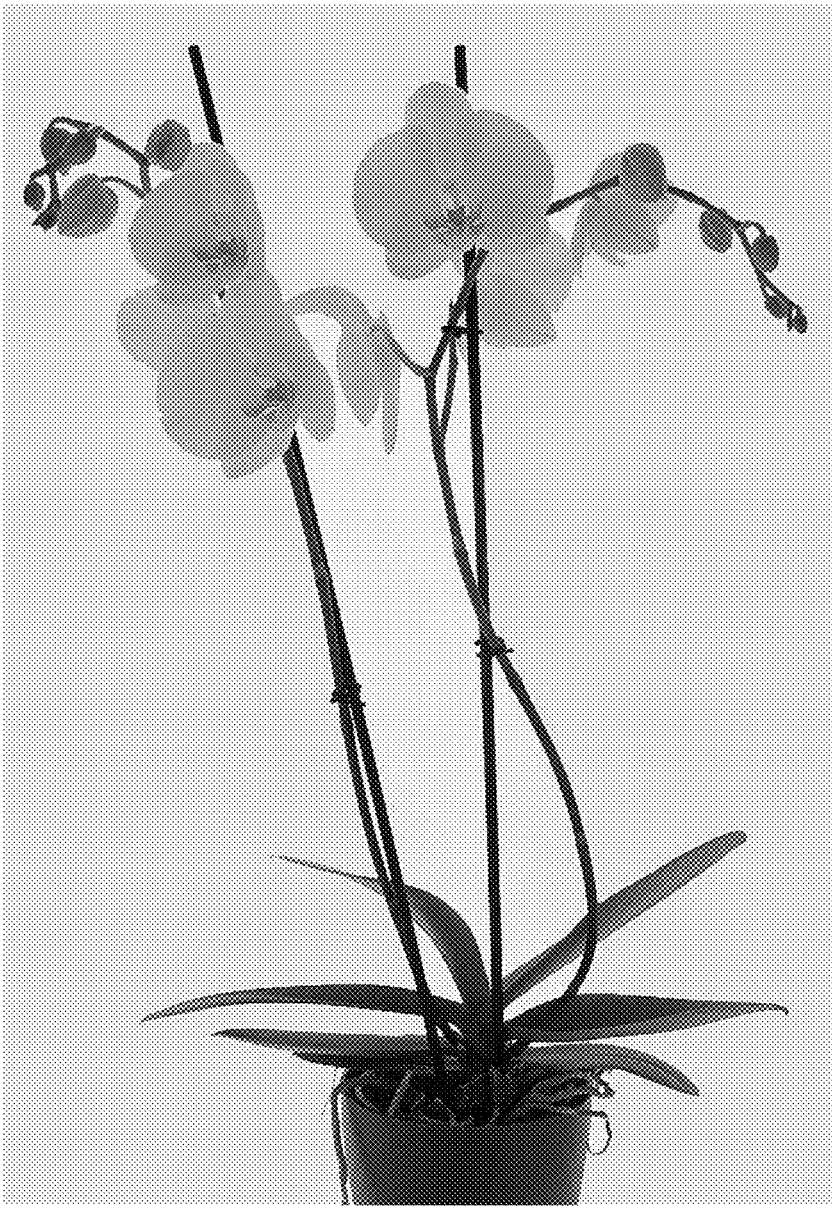

Botanical designation: *Phalaenopsis hybrida.*
Cultivar denomination: 'PHA533378'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B. V. of Bleiswijk, The Netherlands on Apr. 18, 2025, application number 2025/0844. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA533378'.

The new *Phalaenopsis* plant is a product of a planned breeding program conducted by the Inventor in Bleiswijk, The Netherlands. The objective of the breeding program is to develop new freely flowering *Phalaenopsis* plants with white-colored flowers.

The new *Phalaenopsis* plant originated from a cross-pollination in December, 2016 in Bleiswijk, The Netherlands of a proprietary breeding selection of *Phalaenopsis hybrida* identified as code number 00-31849-02, not patented, as the female, or seed, parent with a proprietary breeding selection of *Phalaenopsis hybrida* identified as code number 00001-4911, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in August, 2019.

Asexual reproduction of the new *Phalaenopsis* plant by in vitro meristem propagation in a controlled environment in Bleiswijk, The Netherlands since August, 2019 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA533378'. These characteristics in combination distinguish 'PHA533378' as a new and distinct *Phalaenopsis* plant:

1. Upright plant habit; medium in height.
2. Moderately vigorous growth habit.
3. Sturdy flowering stems.
4. Freely flowering habit with typically two inflorescences developing per plant, each inflorescence with numerous flowers.
5. Medium to broad white-colored flowers.

Plants of the new *Phalaenopsis* can be compared to plants of the female parent selection. Plants of the new *Phalaen-*

*opsis* differ primarily from plants of the female parent selection in the following characteristics:

1. Flowers of plants of the new *Phalaenopsis* are flat in lateral view whereas flowers of plants of the female parent selection are concave in lateral view.
2. The lateral lobes of the labella of plants of the new *Phalaenopsis* are more inwardly curved than the lateral lobes of the labella of plants of the female parent selection.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are semi-erect to horizontal in aspect whereas leaves of plants of the male parent selection are semi-erect to erect in aspect.
2. Leaf apices of plants of the new *Phalaenopsis* are broadly obtuse whereas leaf apices of plants of the male parent selection are acute.

Plants of the new *Phalaenopsis* can be compared to plants of *Phalaenopsis hybrida* 'PHALFOREI', disclosed in U.S. Plant Pat. No. 28,944. In side-by-side comparisons, plants of the new *Phalaenopsis* differ primarily from plants of 'PHALFOREI' in the following characteristics:

1. Plants of the new *Phalaenopsis* are shorter than plants of 'PHALFOREI'.
2. Flower petals of plants of the new *Phalaenopsis* are free whereas flower petals of plants of 'PHALFOREI' are not free and are "touching".

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA533378' grown in a container.

Figure 2:
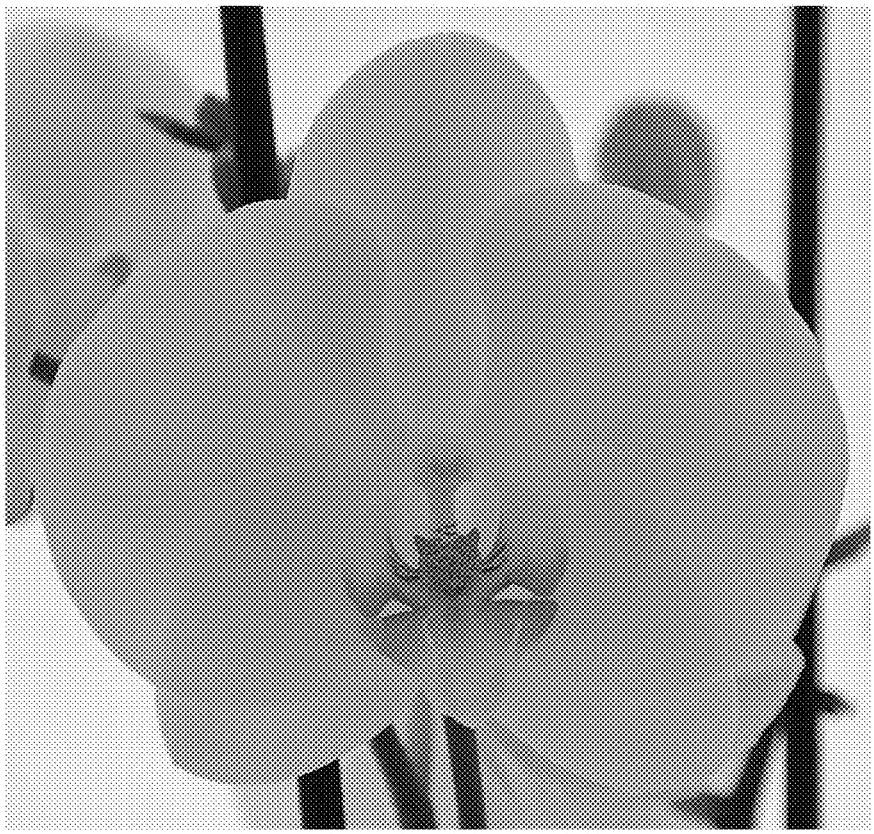

The photograph on the second sheet (FIG. 2) is a close-up view of a typical flower of 'PHA533378'.

DETAILED BOTANICAL DESCRIPTION

The aforementioned photographs and following observations and measurements describe plants grown during the summer in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA533378'.

Parentage:

*Female, or seed, parent*.—Proprietary breeding selection of *Phalaenopsis hybrida* identified as code number 00-31849-02, not patented.

*Male, or pollen, parent*.—Proprietary breeding selection of *Phalaenopsis hybrida* identified as code number 00001-4911, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit; medium in height; typically two inflorescences developing per plant, each inflorescence with numerous flowers; monopodial; and moderately vigorous growth habit.

*Plant height, substrate level to top of foliar plane*.—About 11.5 cm.

*Plant height, substrate level to top of floral plane*.—About 45.6 cm.

*Plant diameter or spread*.—About 35.4 cm.

Leaf description:

*Arrangement and quantity*.—Distichous, simple; sessile; about six to seven fully-developed leaves per plant.

*Length*.—About 17.5 cm.

*Width*.—About 7.7 cm.

*Aspect*.—Semi-erect to horizontal.

*Shape*.—Oblanceolate; slightly carinate.

*Apex*.—Unequal broadly obtuse.

*Base*.—Sheathed. Sheath length: About 1.8 cm. Sheath width: About 1.4 cm. Sheath color: Close to a blend of 144A and 144B.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to 147A; narrow marginal edges, close to N144C. Developing leaves, lower surface: Close to 146B. Fully expanded leaves, upper surface: Close to a blend of 137B and 147A; venation, close to a blend of 137B and 147A. Fully expanded leaves, lower surface: Close to 146B; venation, close to 144A.

Inflorescence description:

*Appearance and flowering habit*.—Showy zygomorphic flowers arranged on axillary simple or branched racemes; typically two inflorescences develop per plant; each inflorescence with about eleven flowers; flowers face outwardly on upright to outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences last for about 18 weeks on the plant; flowers not persistent.

*Inflorescence length* (*lowermost flower to inflorescence apex*).—About 26.2 cm.

*Inflorescence width*.—About 16.3 cm.

*Flower buds*.—Height: About 2.9 cm. Diameter: About 2.1 cm by 2.9 cm. Shape: Broadly ovate. Color: Close to 145C; main vein, close to 151C.

*Flower size*.—About 8.7 cm (vertical) by 9.6 cm (horizontal).

*Flower depth*.—About 3 cm.

*Petals, quantity and arrangement*.—Three, two lateral petals and one center petal transformed into a labellum.

*Lateral petals*.—Length: About 4.9 cm. Width: About 6.1 cm. Shape: Reniform. Apex: Obtuse. Margin: Entire; not undulate. Texture and luster, upper and lower surfaces: Smooth, glabrous; moderately velvety; matte. Color: When opening, upper surface: Close to 155C. When opening, lower surface: Close to 157C; towards the apex and margins, close to NN155A. Fully opened, upper and lower surfaces: Close to NN155D; color does not change with subsequent development.

*Labella*.—Appearance: Three-parted with two lateral lobes and a central lobe; overall shape, broadly cordate to reniform. Length, lateral lobes: About 2.3 cm. Width, lateral lobes: About 1.8 cm. Length, central lobe: About 2.4 cm. Width, central lobe: About 3 mm to 23 mm. Length, cirrhose tips: About 3.3 cm. Shape, lateral lobes: Broadly obovate. Shape, central lobe: Broadly rhomboidal with a slightly elongated apex. Apex, lateral lobes: Obtuse. Apex, central lobe: Obtuse with two cirrhose apices, slightly wavy and pointing upwards and backwards. Margins, lateral and central lobes: Entire. Texture and luster, lateral and central lobes, upper and lower surfaces: Smooth, glabrous; moderately velvety; matte. Callosities: Located at the base of the labellum and attachment point of the lateral petals; about 6 mm in length, about 7 mm in width and about 7 mm in height. Color: When opening, upper surface: Lateral lobes: Close to NN155D; at the base, axial stripes, close to 183B; lower margins, close to a blend of 1A and 154B. Central lobe: Close to NN155D; towards the base, close to 5A; at the base, close to NN155D with radial stripes, close to 187C; narrow distal margins, close to 164A; cirrhose apices, close to NN155D and distally, closer to 150C. Callosities: Close to 155A; towards the apex, close to 9A to 9C with fine dots and stripes, close to 172A. When opening, lower surface: Lateral lobes: Close to NN155D; lower margins, close to a blend of 1A and 154B. Central lobe: Close to NN155D; towards the base, close to 1A and 1B; at the base, close to NN155C; narrow distal margins, close to 164A; cirrhose apices, close to NN155D and distally, closer to 150C. Fully opened, upper surface: Lateral lobes: Close to NN155D; at the base, axial stripes, close to 178B; lower margins, close to 7A. Central lobe: Close to NN155D; towards the base, close to 9B; at the base, close to NN155D with radial stripes, close to 187C; narrow distal margins, close to N170A; cirrhose apices, close to NN155D and distally, closer to 3C. Callosities: Close to 4D; towards the apex, close to 13A to 13B with fine dots and stripes, close to 172A. Fully opened, lower surface: Lateral lobes: Close to NN155D; lower margins, close to 7A. Central lobe: Close to NN155D; towards the base, close to 9C; at the base, close to NN155C; narrow distal margins, close to N170A; cirrhose apices, close to NN155D and distally, closer to 3C.

*Sepals*.—Quantity and arrangement: Three, one upper dorsal sepal and two lower lateral sepals. Length, dorsal sepal: About 5.5 cm. Width, dorsal sepal: About 3.8 cm. Length, lateral sepals: About 5.7 cm. Width, lateral sepals: About 3.3 cm. Shape, dorsal sepal: Broadly elliptic. Shape, lateral sepals: Ovate. Apex, dorsal sepal: Minutely retuse. Apex, lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to 155C. When opening, lower surface: Close to a blend of 145C, 145D and 150D; towards the apex and margins, close to 157D. Fully opened, upper and lower surfaces: Close to NN155D. Color, lateral sepals: When opening, upper surface: Close to 157D; at the base, close to 145D. When opening, lower surface: Close to a blend of 145D and 150D; towards the base, close to 145C; main vein, close to 145B. Fully opened, upper surface: Close to NN155D; at the base, close to 157B. Fully opened, lower surface: Close to 155C; towards the base and apex, close to NN155D; at the base, close to 145D; main vein, close to 157A.

*Peduncles*.—Length: About 55.9 cm. Diameter: About 5 mm. Aspect: Upright to outwardly arching. Texture and luster: Smooth, glabrous; matte. Color: Close to 146A; densely covered with fine dots, close to 146D.

*Pedicels*.—Length: About 4.1 cm. Diameter: About 3 mm. Aspect: About 60° from peduncle axis. Texture and luster: Smooth, glabrous; matte. Color: Close to 144C; distal end, close to 157A; proximal end, close to 146B and 146C.

*Reproductive organs*.—Androecium: Column length: About 9 mm. Column width: About 6 mm. Column color: Close to NN155C. Pollinia quantity: Two. Pollinia diameter (per two pollinia): About 2 mm. Pollinia color: Close to 23A. Gynoecium: Stigma length: About 4 mm. Stigma width: About 5 mm. Stigma shape: Reniform. Stigma color: Close to 155C. Ovary length: About 7 mm. Ovary diameter: About 1 mm. Ovary color: Close to 150B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA533378' as herein illustrated and described.

* * * * *